US012433709B2

(12) United States Patent
McNulty et al.

(10) Patent No.: US 12,433,709 B2
(45) Date of Patent: Oct. 7, 2025

(54) MEDICAL DEVICE PACKAGE WITH FIRST USE INDICATOR LABEL

(71) Applicant: Hollister Incorporated, Libertyville, IL (US)

(72) Inventors: Vivienne McNulty, Dublin (IE); Shane O'Malley, Ballina (IE); Michelle Heffernan, Sligo (IE)

(73) Assignee: Hollister Incorporated, Libertyville, IL (US)

( * ) Notice: Subject to any disclaimer, the term of this patent is extended or adjusted under 35 U.S.C. 154(b) by 123 days.

(21) Appl. No.: 18/043,234

(22) PCT Filed: Sep. 1, 2021

(86) PCT No.: PCT/US2021/048635

§ 371 (c)(1),
(2) Date: Feb. 27, 2023

(87) PCT Pub. No.: WO2022/051346

PCT Pub. Date: Mar. 10, 2022

(65) Prior Publication Data

US 2024/0024059 A1 Jan. 25, 2024

Related U.S. Application Data

(60) Provisional application No. 63/074,596, filed on Sep. 4, 2020.

(51) Int. Cl.
*A61B 50/30* (2016.01)

(52) U.S. Cl.
CPC .......... *A61B 50/30* (2016.02); *A61B 2560/02* (2013.01)

(58) Field of Classification Search
CPC . A61M 25/002; B65D 43/16; B65D 2401/15; B65D 2401/30; B65D 2401/10; B65D 2401/05; B65D 2401/00; B65D 83/224; B65D 55/0827; B65D 5/4233
USPC .................................. 206/807, 247; 220/214
See application file for complete search history.

(56) References Cited

U.S. PATENT DOCUMENTS

| | | | |
|---|---|---|---|
| D137,496 | S | 3/1944 | Lustig |
| D139,383 | S | 11/1944 | Lampl |
| 3,114,455 | A | 12/1963 | Claisse et al. |
| 3,203,545 | A | 8/1965 | Grossman |

(Continued)

FOREIGN PATENT DOCUMENTS

| | | | |
|---|---|---|---|
| AT | 369994 | B | 2/1983 |
| CN | 2078634 | U | 6/1991 |

(Continued)

OTHER PUBLICATIONS

International Search Report and Written Opinion for International Application No. PCT/US2017/028937 dated Aug. 21, 2017.

(Continued)

*Primary Examiner* — Robert Poon
(74) *Attorney, Agent, or Firm* — Cook Alex Ltd.

(57) ABSTRACT

A package (10) for a medical product is provided. The medical package includes a case (12), a cap (14), a hinge (42) that connects the case to the cap and a first use indication label (16) that confirms whether a closed package has been previously opened. The first use indication label spans both an indentation (72) in the cap and an indentation (74) in the case.

6 Claims, 5 Drawing Sheets

(56) References Cited

U.S. PATENT DOCUMENTS 3,369,542 A 2/1968 Thaidgsman
3,794,042 A 2/1974 De Klotz et al.
3,854,483 A 12/1974 Powers
3,867,945 A 2/1975 Long
3,894,540 A 7/1975 Bonner, Jr.
3,920,023 A 11/1975 Dye et al.
3,934,722 A 1/1976 Goldberg
4,043,345 A 8/1977 Kramann et al.
4,109,659 A 8/1978 Sheridan
4,248,214 A 2/1981 Hannah et al.
4,432,758 A 2/1984 Finegold
4,462,504 A 7/1984 Roth et al.
4,553,959 A 11/1985 Hickey et al.
4,684,369 A 8/1987 Wildemeersch
4,773,901 A 9/1988 Norton
4,898,586 A 2/1990 McDonough
4,935,017 A 6/1990 Sylvanowicz
4,956,298 A 9/1990 Diekmann
5,012,940 A 5/1991 Koehn
5,084,036 A 1/1992 Rosenbaum
D327,327 S 6/1992 Deguchi et al.
5,149,326 A 9/1992 Woodgrift et al.
5,217,114 A 6/1993 Gadberry et al.
5,225,165 A 7/1993 Perlman
5,358,136 A 10/1994 Rubendall
5,380,270 A 1/1995 Ahmadzadeh
5,413,561 A 5/1995 Fischell et al.
5,417,326 A 5/1995 Winer
5,582,599 A 12/1996 Daneshvar
D381,422 S 7/1997 Erskine et al.
D383,538 S 9/1997 Erskine et al.
5,860,550 A * 1/1999 Miller .................... B65D 25/54 220/4.23
5,868,265 A 2/1999 Kobayahi
5,881,774 A 3/1999 Utterberg
5,919,170 A 7/1999 Woessner
6,186,325 B1 2/2001 Schmidt
6,258,078 B1 7/2001 Thilly
D449,104 S 10/2001 Baker et al.
6,328,355 B1 12/2001 Bortz
6,439,410 B1 8/2002 Dubach
6,460,712 B2 10/2002 Smith et al.
6,460,726 B1 10/2002 Hierzer et al.
6,585,721 B2 7/2003 Fiore
6,634,498 B2 10/2003 Kayerod et al.
D488,863 S 4/2004 Quinn
6,822,253 B1 11/2004 Martin et al.
6,871,753 B2 3/2005 McHutchinson
6,908,013 B2 6/2005 Thomson et al.
6,908,113 B2 6/2005 Chaduc et al.
6,926,708 B1 8/2005 Franks-Farah et al.
D509,352 S 9/2005 Raven et al.
6,964,336 B2 11/2005 Harrold
7,120,487 B2 10/2006 Nelson
7,134,575 B2 11/2006 Vogel et al.
7,306,128 B2 12/2007 Eimer
7,311,698 B2 12/2007 Tanghoj et al.
7,353,969 B2 4/2008 McHutchinson
D577,813 S 9/2008 Seki et al.
D577,814 S 9/2008 Seki et al.
7,438,704 B1 10/2008 Kawashima et al.
D584,408 S 1/2009 Castellani
D584,409 S 1/2009 Miller et al.
D584,410 S 1/2009 Miller et al.
D588,797 S 3/2009 Tanghoej et al.
7,546,931 B2 6/2009 Giusti
D595,847 S 7/2009 Miller et al.
7,571,804 B2 8/2009 Kjellmann Bruun et al.
7,614,514 B2 11/2009 Fuchs
7,624,868 B2 12/2009 Booker et al.
7,655,063 B2 2/2010 Wang et al.
7,682,353 B2 3/2010 Tanghoj et al.
D614,396 S 4/2010 Tanghoej et al.
7,699,168 B2 4/2010 Ryan et al.
7,717,284 B2 5/2010 Giusti
7,748,550 B2 7/2010 Cho
D630,733 S 1/2011 Ahlgren
7,867,220 B2 1/2011 Tanghoj
7,886,907 B2 2/2011 Murray et al.
7,967,744 B2 6/2011 Kaye et al.
7,992,737 B2 8/2011 Salice
8,069,980 B2 12/2011 Stopek et al.
8,137,309 B2 3/2012 Nishtala et al.
8,172,101 B2 5/2012 Giusti
8,181,778 B1 5/2012 van Groningen et al.
8,230,993 B2 7/2012 Tanghoej
8,282,624 B2 10/2012 Tanghoej et al.
8,292,110 B2 10/2012 Rutter et al.
D673,264 S 12/2012 Kunze
8,361,057 B2 1/2013 Tanghoej et al.
8,381,925 B2 2/2013 Skillin et al.
8,398,615 B2 3/2013 Torstensen et al.
8,434,639 B2 5/2013 Markert
8,439,213 B2 5/2013 Goria et al.
8,448,798 B2 5/2013 Groubert et al.
8,491,568 B2 7/2013 Schertiger et al.
8,511,472 B2 8/2013 Dupuis et al.
8,523,843 B2 9/2013 Kavanagh et al.
8,529,549 B2 9/2013 Tanghoj et al.
D691,365 S 10/2013 Cote
8,579,115 B2 11/2013 Murphy et al.
8,597,245 B2 12/2013 Jeter et al.
8,616,406 B1 12/2013 Sawicki
8,616,407 B2 12/2013 Sawicki
D705,925 S 5/2014 Murray et al.
8,733,566 B2 5/2014 Druitt et al.
D707,351 S 6/2014 Kunze
8,752,722 B2 6/2014 Kuhn et al.
8,863,968 B2 10/2014 Giusti
D724,199 S 3/2015 Bambot et al.
9,033,149 B2 5/2015 Terry
9,090,386 B2 * 7/2015 van Alfen .............. B65D 43/16
D738,973 S 9/2015 Dingman
D739,932 S 9/2015 Ratjen et al.
9,169,048 B2 10/2015 Ludewigs et al.
9,220,866 B2 12/2015 Van Groningen et al.
D747,184 S 1/2016 Murray et al.
9,277,966 B2 3/2016 Seitz, III
9,334,097 B2 5/2016 Skillin et al.
9,352,318 B2 5/2016 Giusti
D760,490 S 7/2016 Johnson
9,415,909 B2 8/2016 Druitt et al.
9,422,089 B2 8/2016 Wheeler
9,501,958 B2 11/2016 Pietarinen et al.
9,511,906 B2 12/2016 van Alfen et al.
9,650,184 B2 * 5/2017 Fily .................... B65D 47/0838
9,669,187 B2 6/2017 Tjassens et al.
9,687,629 B1 6/2017 Palmer
9,701,451 B2 7/2017 Skillin et al.
D796,025 S 8/2017 Lo
10,857,068 B2 12/2020 Davis et al.
2001/0001443 A1 5/2001 Kayerod et al.
2001/0037954 A1 11/2001 Schmidt et al.
2003/0004496 A1 1/2003 Tanghoj
2003/0060807 A1 3/2003 Tanghoj et al.
2003/0141210 A1 7/2003 Yanke et al.
2004/0016714 A1 1/2004 Wood et al.
2004/0150221 A1 8/2004 Brown
2004/0158231 A1 8/2004 Tanghoj et al.
2005/0043715 A1 2/2005 Nestenborg et al.
2005/0067366 A1 3/2005 Dubach
2005/0106339 A1 5/2005 Baker
2005/0106340 A1 5/2005 Baker
2006/0043052 A1 * 3/2006 Lin .................... B65D 47/0838 215/253
2006/0091670 A1 5/2006 Gaynor
2006/0116661 A1 6/2006 Tanghoej
2006/0142737 A1 6/2006 Tanghoj
2006/0180585 A1 8/2006 Cunningham et al.
2007/0034537 A1 2/2007 Fago et al.
2007/0068977 A1 3/2007 Vogel et al.
2008/0033371 A1 2/2008 Updegraff et al.
2008/0156805 A1 * 7/2008 Perry ................... B65D 51/247 220/361

(56) References Cited

U.S. PATENT DOCUMENTS

| | | | | |
|---|---|---|---|---|
| 2008/0183181 | A1 | 7/2008 | Treacy et al. | |
| 2008/0264961 | A1 | 10/2008 | Sawyer | |
| 2008/0289984 | A1 | 11/2008 | Raven et al. | |
| 2008/0319423 | A1 | 12/2008 | Tanghoj et al. | |
| 2009/0008279 | A1 | 1/2009 | Tanghoej | |
| 2009/0054876 | A1 | 2/2009 | Borodulin et al. | |
| 2009/0166361 | A1 | 7/2009 | Lourenco | |
| 2009/0299334 | A1 | 12/2009 | Nishtala et al. | |
| 2010/0087801 | A1 | 4/2010 | Torstensen et al. | |
| 2010/0106236 | A1 | 4/2010 | Nelson | |
| 2010/0211050 | A1 | 8/2010 | Luther | |
| 2010/0224643 | A1 | 9/2010 | Daggett | |
| 2010/0252469 | A1 | 10/2010 | Tanghoej | |
| 2010/0256580 | A1 | 10/2010 | Faber | |
| 2010/0324540 | A1 | 12/2010 | Paulen et al. | |
| 2011/0060317 | A1 | 3/2011 | Frojd | |
| 2011/0224653 | A1 | 9/2011 | Torstensen | |
| 2012/0016318 | A1 | 1/2012 | Hoang et al. | |
| 2012/0051967 | A1 | 3/2012 | Murphy et al. | |
| 2012/0165791 | A1 | 6/2012 | Lovmar et al. | |
| 2012/0179144 | A1 | 7/2012 | Carleo | |
| 2012/0271281 | A1 | 10/2012 | Schertiger | |
| 2013/0068767 | A1 | 3/2013 | Fraser et al. | |
| 2013/0134123 | A1 | 5/2013 | Fraser et al. | |
| 2013/0150828 | A1 | 6/2013 | Conway | |
| 2013/0161344 | A1 | 6/2013 | Park et al. | |
| 2013/0186791 | A1 | 7/2013 | Triquigneaux | |
| 2013/0218136 | A1 | 8/2013 | Tanghoej et al. | |
| 2013/0220967 | A1* | 8/2013 | Wang | B65D 47/0838 215/253 |
| 2013/0240393 | A1 | 9/2013 | Bode et al. | |
| 2013/0261608 | A1 | 10/2013 | Tanghoj | |
| 2013/0289537 | A1 | 10/2013 | Schertiger et al. | |
| 2013/0292286 | A1 | 11/2013 | Van Groningen et al. | |
| 2013/0299516 | A1 | 11/2013 | Dupuis et al. | |
| 2013/0327664 | A1 | 12/2013 | Tanghoj | |
| 2014/0262860 | A1 | 9/2014 | Hagel | |
| 2014/0262903 | A1 | 9/2014 | Mitten et al. | |
| 2014/0263436 | A1 | 9/2014 | Gelov et al. | |
| 2014/0360896 | A1 | 12/2014 | Torstensen | |
| 2015/0352321 | A1 | 12/2015 | Hannon et al. | |
| 2016/0016703 | A1 | 1/2016 | Muhlemann | |
| 2016/0023818 | A1 | 1/2016 | Gelov et al. | |
| 2016/0059999 | A1 | 3/2016 | Fraser et al. | |
| 2016/0172742 | A1 | 6/2016 | Forster | |
| 2016/0193447 | A1 | 7/2016 | Mattiassen | |
| 2016/0228872 | A1 | 8/2016 | Giusti | |
| 2016/0325895 | A1 | 11/2016 | Browning, Jr. | |
| 2016/0332789 | A1 | 11/2016 | Yerecic | |
| 2017/0014597 | A1 | 1/2017 | Hagel | |
| 2017/0080177 | A1 | 3/2017 | Tanghoej et al. | |
| 2017/0107365 | A1 | 4/2017 | Rycrift et al. | |
| 2017/0166369 | A1 | 6/2017 | Mitten et al. | |
| 2017/0173300 | A1 | 6/2017 | Hannon et al. | |
| 2017/0175428 | A1 | 6/2017 | Quinn et al. | |
| 2017/0267438 | A1* | 9/2017 | Welch | A45C 11/20 |
| 2017/0305630 | A1* | 10/2017 | Miller | B65C 3/08 |
| 2017/0326334 | A1 | 11/2017 | Terry | |
| 2018/0079568 | A1* | 3/2018 | Shmeltzer | B65D 43/0239 |
| 2019/0151605 | A1 | 5/2019 | McMenamin et al. | |
| 2020/0230349 | A1* | 7/2020 | McMenamin | B65D 43/162 |

FOREIGN PATENT DOCUMENTS

| | | | |
|---|---|---|---|
| CN | 2340720 | Y | 9/1999 |
| DE | 20117438 | U1 | 3/2002 |
| DE | 10213411 | A1 | 10/2003 |
| DE | 20317135 | U1 | 1/2004 |
| DE | 202005008071 | U1 | 7/2005 |
| DE | 102004013712 | B3 | 8/2005 |
| DE | 202005009946 | U1 | 9/2005 |
| DE | 202006013663 | U1 | 11/2006 |
| DE | 202010006267 | U1 | 11/2010 |
| DE | 202010007433 | U1 | 6/2011 |
| DE | 202011107025 | U1 | 1/2013 |
| DE | 202011107059 | U1 | 1/2013 |
| DE | 102013014483 | A1 | 6/2014 |
| DE | 202017101126 | U1 | 3/2017 |
| DE | 102016205834 | B3 | 5/2017 |
| DK | 173714 | A | 5/2000 |
| EP | 0041487 | A | 12/1981 |
| EP | 0134630 | A | 3/1985 |
| EP | 0781572 | A2 | 7/1997 |
| EP | 0861639 | A2 | 9/1998 |
| EP | 0910425 | A1 | 4/1999 |
| EP | 0923398 | A1 | 6/1999 |
| EP | 0812287 | B1 | 11/1999 |
| EP | 0996542 | A1 | 5/2000 |
| EP | 1023882 | A1 | 8/2000 |
| EP | 0933304 | B1 | 3/2003 |
| EP | 1086024 | B1 | 5/2003 |
| EP | 1334039 | A1 | 8/2003 |
| EP | 1466645 | A2 | 10/2004 |
| EP | 1174359 | B1 | 5/2005 |
| EP | 1392575 | B1 | 9/2005 |
| EP | 1593710 | A1 | 11/2005 |
| EP | 1607344 | A1 | 12/2005 |
| EP | 1615960 | A1 | 1/2006 |
| EP | 1317382 | B1 | 3/2006 |
| EP | 1634554 | A2 | 3/2006 |
| EP | 1638856 | A1 | 3/2006 |
| EP | 1671663 | A1 | 6/2006 |
| EP | 1696990 | A1 | 9/2006 |
| EP | 1487712 | B1 | 10/2006 |
| EP | 1720772 | A1 | 11/2006 |
| EP | 1278679 | B1 | 6/2007 |
| EP | 1863719 | A2 | 12/2007 |
| EP | 1799574 | B1 | 1/2008 |
| EP | 1878461 | A1 | 1/2008 |
| EP | 1897579 | A1 | 3/2008 |
| EP | 1897580 | A1 | 3/2008 |
| EP | 1409369 | B1 | 7/2008 |
| EP | 1963195 | A2 | 9/2008 |
| EP | 1979032 | A1 | 10/2008 |
| EP | 1982741 | A2 | 10/2008 |
| EP | 1986921 | A1 | 11/2008 |
| EP | 2042211 | A1 | 4/2009 |
| EP | 2044963 | A1 | 4/2009 |
| EP | 2060296 | A1 | 5/2009 |
| EP | 2072075 | A1 | 6/2009 |
| EP | 2106821 | A1 | 10/2009 |
| EP | 1858575 | B1 | 5/2010 |
| EP | 2035292 | B1 | 5/2010 |
| EP | 2251454 | A2 | 11/2010 |
| EP | 2292294 | A1 | 3/2011 |
| EP | 2295108 | A1 | 3/2011 |
| EP | 2308543 | A1 | 4/2011 |
| EP | 1966058 | B1 | 7/2011 |
| EP | 2450076 | A1 | 5/2012 |
| EP | 2468319 | A1 | 6/2012 |
| EP | 2325100 | B1 | 8/2012 |
| EP | 2504054 | A1 | 10/2012 |
| EP | 2515985 | A1 | 10/2012 |
| EP | 2596831 | A2 | 5/2013 |
| EP | 2242696 | B1 | 6/2013 |
| EP | 2617316 | A2 | 7/2013 |
| EP | 2638927 | A2 | 9/2013 |
| EP | 2682069 | A1 | 1/2014 |
| EP | 2686054 | A1 | 1/2014 |
| EP | 2750748 | A1 | 7/2014 |
| EP | 2250102 | B1 | 9/2014 |
| EP | 2774648 | A1 | 9/2014 |
| EP | 2785409 | A1 | 10/2014 |
| EP | 2823845 | A1 | 1/2015 |
| EP | 2782842 | B1 | 7/2015 |
| EP | 3033279 | A1 | 6/2016 |
| EP | 3038075 | A2 | 6/2016 |
| EP | 2576374 | B1 | 9/2016 |
| EP | 3113922 | A1 | 1/2017 |
| EP | 2605977 | B1 | 5/2017 |
| EP | 3210909 | A1 | 8/2017 |
| EP | 3248620 | A1 | 11/2017 |
| EP | 3476758 | A1 | 5/2019 |

(56) References Cited

FOREIGN PATENT DOCUMENTS

| | | | |
|---|---|---|---|
| FR | 2717676 | A1 | 9/1995 |
| FR | 2801567 | A3 | 6/2001 |
| GB | 2031735 | A | 4/1980 |
| GB | 2033231 | A | 5/1980 |
| GB | 2322079 | A | 8/1988 |
| JP | 2001025473 | A | 1/2001 |
| KR | 20110101674 | A | 9/2011 |
| PT | 2216064 | T | 9/2016 |
| SE | 514121 | C2 | 1/2001 |
| WO | 9608219 | A1 | 3/1996 |
| WO | 9726937 | A1 | 7/1997 |
| WO | 9741811 | A1 | 11/1997 |
| WO | 9811932 | A1 | 3/1998 |
| WO | 9819729 | A1 | 5/1998 |
| WO | 9930761 | A1 | 6/1999 |
| WO | 9942155 | A2 | 8/1999 |
| WO | 0016843 | A1 | 3/2000 |
| WO | 0030575 | A1 | 6/2000 |
| WO | 0047494 | A1 | 8/2000 |
| WO | 0143807 | A1 | 6/2001 |
| WO | 0160255 | A1 | 8/2001 |
| WO | 02060361 | A2 | 8/2002 |
| WO | 02080843 | A2 | 10/2002 |
| WO | 03001994 | A1 | 1/2003 |
| WO | 03008028 | A2 | 1/2003 |
| WO | 03008029 | A2 | 1/2003 |
| WO | 03022561 | A1 | 3/2003 |
| WO | 03045487 | A2 | 6/2003 |
| WO | 03061732 | A2 | 7/2003 |
| WO | 03092779 | A1 | 11/2003 |
| WO | 03097237 | A2 | 11/2003 |
| WO | 2004021890 | A1 | 3/2004 |
| WO | 2004032750 | A1 | 4/2004 |
| WO | 2004035123 | A1 | 4/2004 |
| WO | 2004050155 | A1 | 6/2004 |
| WO | 2004054446 | A1 | 7/2004 |
| WO | 2004054653 | A1 | 7/2004 |
| WO | 2004056414 | A1 | 7/2004 |
| WO | 2004089454 | A1 | 10/2004 |
| WO | 2004103153 | A2 | 12/2004 |
| WO | 2005014055 | A2 | 2/2005 |
| WO | 2005056414 | A1 | 6/2005 |
| WO | 2005092418 | A1 | 10/2005 |
| WO | 2006005349 | A2 | 1/2006 |
| WO | 2006017439 | A2 | 2/2006 |
| WO | 2006044249 | A2 | 4/2006 |
| WO | 2006044621 | A2 | 4/2006 |
| WO | 2006045809 | A1 | 5/2006 |
| WO | 2006092150 | A1 | 9/2006 |
| WO | 2006121183 | A1 | 11/2006 |
| WO | 2007005851 | A2 | 1/2007 |
| WO | 2007022223 | A2 | 2/2007 |
| WO | 2007038988 | A1 | 4/2007 |
| WO | 2007050685 | A2 | 4/2007 |
| WO | 2007081264 | A1 | 7/2007 |
| WO | 2007082540 | A1 | 7/2007 |
| WO | 2008089081 | A1 | 7/2007 |
| WO | 2007106356 | A2 | 9/2007 |
| WO | 2007106431 | A2 | 9/2007 |
| WO | 2007111891 | A2 | 10/2007 |
| WO | 2007121137 | A2 | 10/2007 |
| WO | 2008024136 | A1 | 2/2008 |
| WO | 2008030999 | A2 | 3/2008 |
| WO | 2008039910 | A2 | 4/2008 |
| WO | 2008090551 | A2 | 7/2008 |
| WO | 2008137353 | A1 | 11/2008 |
| WO | 2009010975 | A1 | 1/2009 |
| WO | 2009017541 | A1 | 2/2009 |
| WO | 2009068043 | A2 | 6/2009 |
| WO | 2009126081 | A1 | 10/2009 |
| WO | 2009139878 | A1 | 11/2009 |
| WO | 2010006620 | A1 | 1/2010 |
| WO | 2010130261 | A1 | 11/2010 |
| WO | 2011011023 | A1 | 1/2011 |
| WO | 2011019359 | A1 | 2/2011 |
| WO | 2011026929 | A1 | 3/2011 |
| WO | 2011034911 | A1 | 3/2011 |
| WO | 2011079129 | A1 | 6/2011 |
| WO | 2011147803 | A1 | 12/2011 |
| WO | 2012006629 | A2 | 1/2012 |
| WO | 2012013662 | A1 | 2/2012 |
| WO | 2012016179 | A1 | 2/2012 |
| WO | 2012016570 | A2 | 2/2012 |
| WO | 2012016571 | A2 | 2/2012 |
| WO | 2012060699 | A1 | 5/2012 |
| WO | 2012079590 | A1 | 6/2012 |
| WO | 2012085107 | A2 | 6/2012 |
| WO | 2012110755 | A2 | 8/2012 |
| WO | 2012134804 | A1 | 10/2012 |
| WO | 2012154946 | A1 | 11/2012 |
| WO | 2012156478 | A1 | 11/2012 |
| WO | 2012166045 | A1 | 12/2012 |
| WO | 2012166967 | A1 | 12/2012 |
| WO | 2013029620 | A1 | 3/2013 |
| WO | 2013029621 | A1 | 3/2013 |
| WO | 2013029622 | A1 | 3/2013 |
| WO | 2013075725 | A1 | 5/2013 |
| WO | 2013083137 | A1 | 6/2013 |
| WO | 2013098190 | A1 | 7/2013 |
| WO | 2013105091 | A1 | 7/2013 |
| WO | 2014062223 | A1 | 4/2014 |
| WO | 2014062225 | A1 | 4/2014 |
| WO | 2014063711 | A1 | 5/2014 |
| WO | 2014074141 | A1 | 5/2014 |
| WO | 2014074147 | A1 | 5/2014 |
| WO | 2014081859 | A1 | 5/2014 |
| WO | 2014085597 | A1 | 6/2014 |
| WO | 2014093056 | A1 | 6/2014 |
| WO | 2014139767 | A1 | 9/2014 |
| WO | 2014140328 | A1 | 9/2014 |
| WO | 2014142895 | A1 | 9/2014 |
| WO | 2014142917 | A1 | 9/2014 |
| WO | 2014142923 | A1 | 9/2014 |
| WO | 2014142930 | A1 | 9/2014 |
| WO | 2014144714 | A1 | 9/2014 |
| WO | 2014145211 | A2 | 9/2014 |
| WO | 2014147620 | A1 | 9/2014 |
| WO | 2014149276 | A1 | 9/2014 |
| WO | 2014159869 | A2 | 10/2014 |
| WO | 2014165046 | A1 | 10/2014 |
| WO | 2014165049 | A1 | 10/2014 |
| WO | 2014176486 | A1 | 10/2014 |
| WO | 2014176867 | A1 | 11/2014 |
| WO | 2014187514 | A1 | 11/2014 |
| WO | 2015065725 | A1 | 5/2015 |
| WO | 2015066673 | A1 | 5/2015 |
| WO | 2015075841 | A1 | 5/2015 |
| WO | 2015120119 | A1 | 8/2015 |
| WO | 2015184365 | A1 | 12/2015 |
| WO | 2016044379 | A2 | 3/2016 |
| WO | 2016094606 | A1 | 6/2016 |
| WO | 2017024106 | A1 | 2/2017 |
| WO | 2017174715 | A1 | 10/2017 |
| WO | 2017185029 | A1 | 10/2017 |
| WO | 2017185052 | A1 | 10/2017 |
| WO | 2018156589 | A2 | 8/2018 |
| WO | 2019010154 | A1 | 1/2019 |
| WO | 2019083839 | A1 | 5/2019 |

OTHER PUBLICATIONS

Urinary Incontinence Applicance, Aids and Equipment, R.N.P. Carroll, retrieved on Apr. 3, 2014 from http://link.springer.com/chapter/10.1007/978-1-4471-1461-1_6# dated Dec. 31, 1992.

International Search Report dated Feb. 24, 2015, for International Application No. PCT/US2014/053573.

International Search Report and Written Opinion for International Application No. PCT/US2015/033344 dated Mar. 12, 2015.

International Search Report and Written Opinion for International Application No. PCT/US2017/028979 dated Aug. 25, 2017.

Total Body Relief and Hygiene for Travel, Home bath, and life's less comfortable moments. "http://www.biorelief.com/blog/self-cath-fits-in-your-pocket/" dated Apr. 19, 2014.

(56) References Cited

OTHER PUBLICATIONS

For Safety: Tamper Evidence by Rondo, pp. 1-3.
International Search Report and Written Opinion for PCT/US2021/048635 Dated Jan. 13, 2022.
International Search Report and Written Opinion for International Application No. PCT/US2018/018965 Dated Sep. 24, 2018.
International Preliminary Report on Patentability for PCT/US2021/048635 Dated Jan. 13, 2022.

* cited by examiner

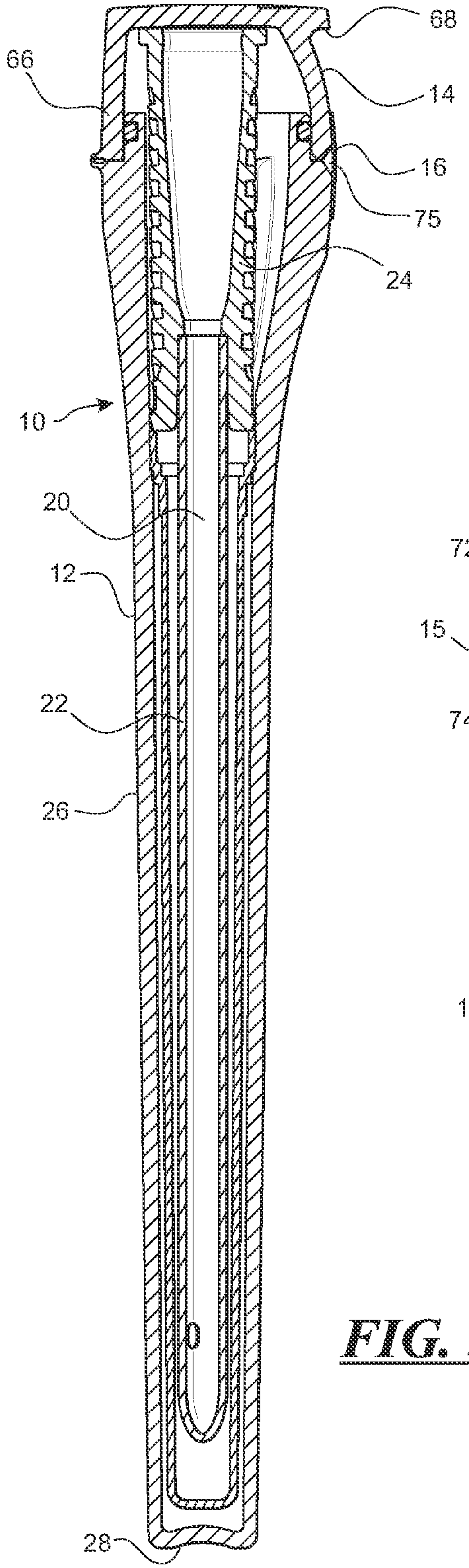
FIG. 3
FIG. 4
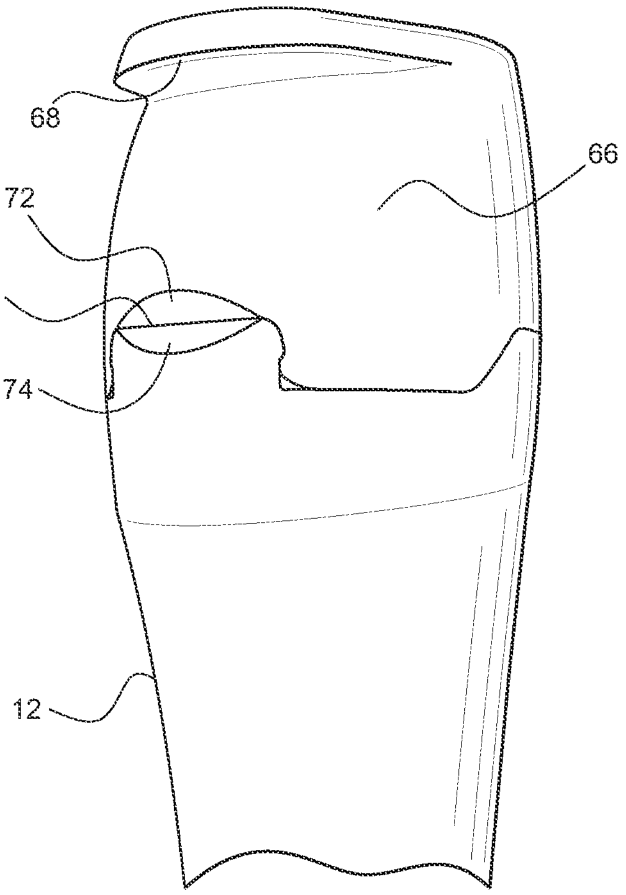

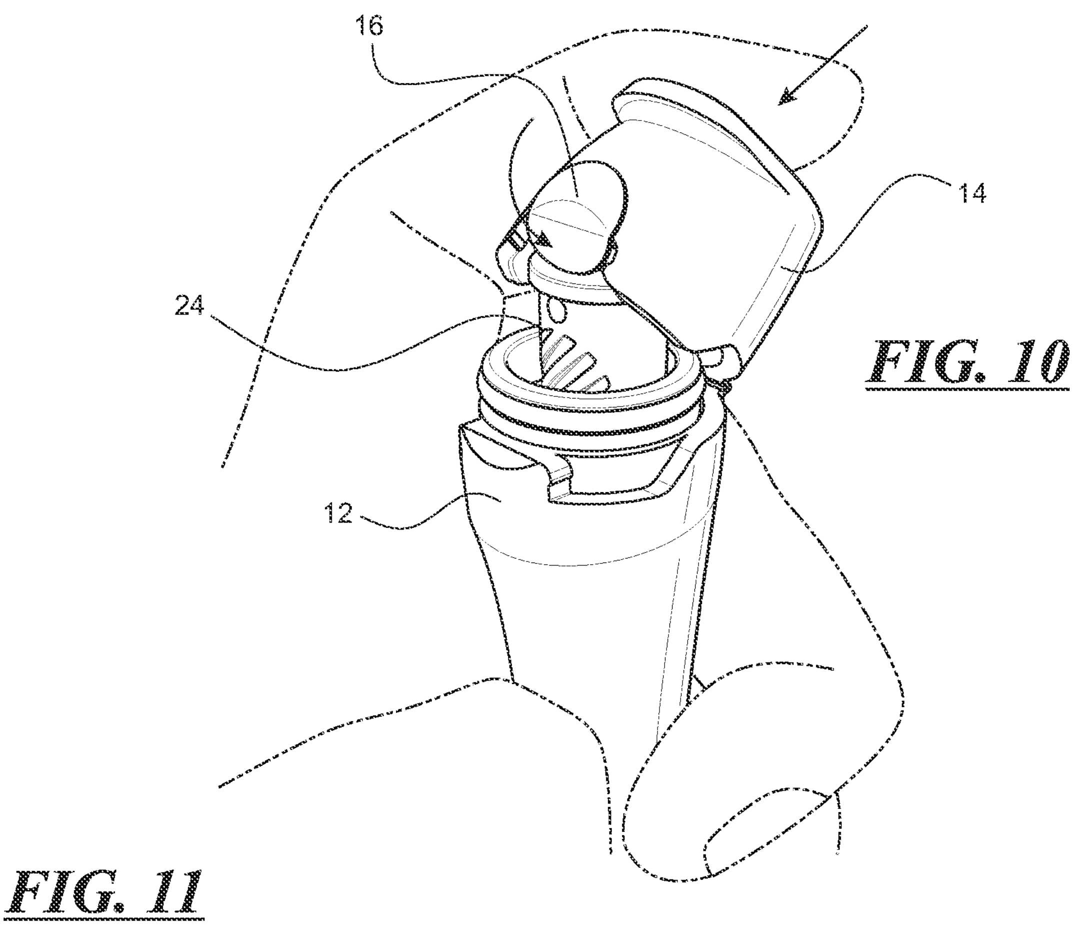
FIG. 10
FIG. 11
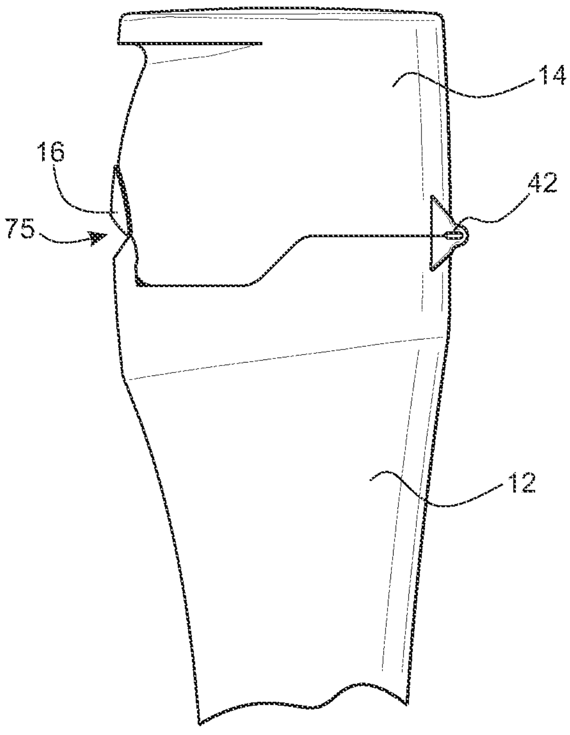
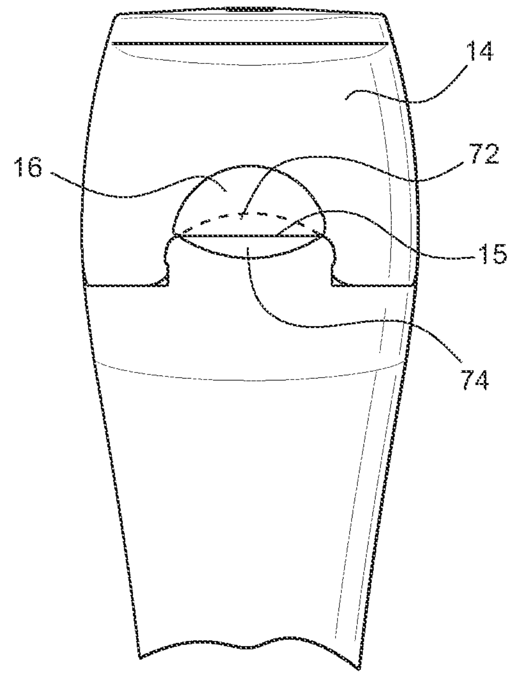
FIG. 12

MEDICAL DEVICE PACKAGE WITH FIRST USE INDICATOR LABEL

CROSS-REFERENCE TO RELATED APPLICATIONS

The present application is the U.S. National Stage Application of PCT Application No. PCT/US2021/048635, filed Sep. 1, 2021, which claims the benefit of and priority to U.S. Provisional Patent Application Ser. No. 63/074,596, filed Sep. 4, 2020 the content of which is incorporated herein by reference.

FIELD OF THE DISCLOSURE

The present disclosure is directed to medical device packages that provide an indication that the package has been previously opened. More particularly, the present disclosure is directed to a medical device package that includes a first use indicator label that assumes a configuration after the package is re-closed or re-sealed. Even more particularly, the present disclosure is directed to a medical device package having a flip cap and a first use indicator label that is carried by the cap.

BACKGROUND

Intermittent catheterization is a good option for many users who suffer from a neurogenic bladder, that is, an atonic or unstable bladder associated with a neurological condition, such as diabetes, stroke, or spinal cord injury. Very often a neurogenic bladder is caused by conditions which may also result in diminished dexterity of the user.

Commonly, in intermittent catheterization, single use, individually packaged, sterile catheters are used. Such catheters are often packaged in a disposable container, Users will often prefer to return a used catheter to their purse or bag for subsequent disposal. Accordingly, the catheter package should be capable of receiving a used catheter back in the package and then being reclosed in a sealed and secured manner. Thus, a catheter package with a reliably re-closable cap would also be desired, Convenience may be further enhanced if the re-closable cap is attached to the remainder of the package, so the cap does not become misplaced during use of the catheter.

One challenge for package designers is the need to provide confirmation to the user whether or not a package has been previously opened. This challenge is heightened where the matching outside geometry of the case and cap makes it difficult to tell whether they have been previously opened, even if a tell-tale label of some sort is initially attached to the case and cap. Confirmation as to whether the seal on a package has been breached (either by intentional use of the product or by accidental opening) is highly desirable as, if the seal has been breached, then the products sterility could be compromised. It is known to apply to the package a first use indicator label that spans the separation line of the cap and case. The label will then tear upon first opening of the package. However, when the label is fully supported by underlying structure, it has been found that the label can tear so cleanly that upon reclosing of the cap the adjoining pieces of the torn label fit back together so well as to make the tear line difficult to see. In this case there are no obvious signs that the cap has been opened, despite the initial tearing of the label.

One example of a catheter package with a first use indicator label is described in WO 2018/156589. The package described therein includes a flip cap attached to an elongated case. The case or the cap includes an indentation or chamfer over which a scored label is placed. The label spans the adjacent areas and surfaces of the cap and case such that when the package is opened (by flipping open the cap), the label is torn or otherwise ruptures to provide an indication that the package has been opened.

While the first use indicator described in WO 2018/156589 has worked satisfactorily, efforts continue to provide reliable first use indication in medical and other packaging.

SUMMARY

There are several aspects to the subject matter disclosed herein.

In one aspect, the present disclosure is directed to a medical device package. The package includes a case for receiving a medical device wherein the case has an open end. The package also includes a cap for sealing the open end of the case. A hinge having one end connected to the cap and a second end connected to the case allows for opening and closing of the case. The outer surface of the cap includes an indentation having a reduced outer dimension compared to the rest of the outer surface in which it is formed. Similarly, the outer surface of the case also includes an indentation having a reduced outer dimension compared to the rest of the outer surface in which it is formed. The indentations in the cap and case are adjacent to each other when the cap is in a fully closed position. A first use indicator label is affixed to the cap and case over the indentations.

In another aspect, the present disclosure is directed to a medical device package including a case for receiving a medical device wherein the case has an open end, and a cap for sealing the open end of the case. The package includes a hinge having one end connected to the cap and a second end connected to said case for selective opening and closing of the package. The package further includes an indentation in the outer surface of the cap, the indentation having a reduced outer dimension compared to the rest of the outer surface in which it is formed, and an indentation in the outer surface of the case, the indentation having a reduced outer dimension compared to the rest of the outer surface in which it is formed. The indentations in the cap and case are adjacent to each other when the cap is in a fully closed position. A first use indicator label is affixed to the cap and covers only the indentation in the cap, and wherein only the indentation in the case is visible.

In yet another aspect, the present disclosure is directed to a medical product assembly including a package, wherein the package includes a case for receiving a medical product, the case having an open end, and a cap for sealing the open end of the case. A hinge having one end connected to the cap and a second end connected to said case allows for opening and closing of the package.

The package includes an indentation in the outer surface of the cap, the indentation having a reduced outer dimension compared to the rest of the outer surface in which it is formed and an indentation in the outer surface of the case, the indentation in the case likewise having a reduced outer dimension compared to the rest of the outer surface in which it is formed. The indentations in the cap and case are adjacent to each other when the cap is in a fully closed position. A first use indicator label is affixed to the cap and case and spans both the indentation in the cap and the indentation in the case. The medical product assembly further includes a medical device contained within the package. The medical device has a distal end that extends beyond the open end of the case. The device is positioned within the case such that a portion of the first use indicator label contacts the distal end of the medical device when the cap is moved from an open position to a re-closed position.

BRIEF DESCRIPTION OF THE DRAWINGS

FIG. 3 is cross-sectional side view of the medical product package with a medical device contained therein;

FIG. 4 is an enlarged perspective view of the medical product package without the first use indicator label;

FIG. 10 is a partial perspective view of the medical product with the cap being closed by a user and the first use indicator label beginning to fold;

FIG. 11 is a partial side view of the medical product package in a fully closed position after initial opening: and FIG. 12 is a partial front view of the medical product package in the fully closed position after an initial opening.

DETAILED DESCRIPTION OF THE EMBODIMENTS

Figure 1:
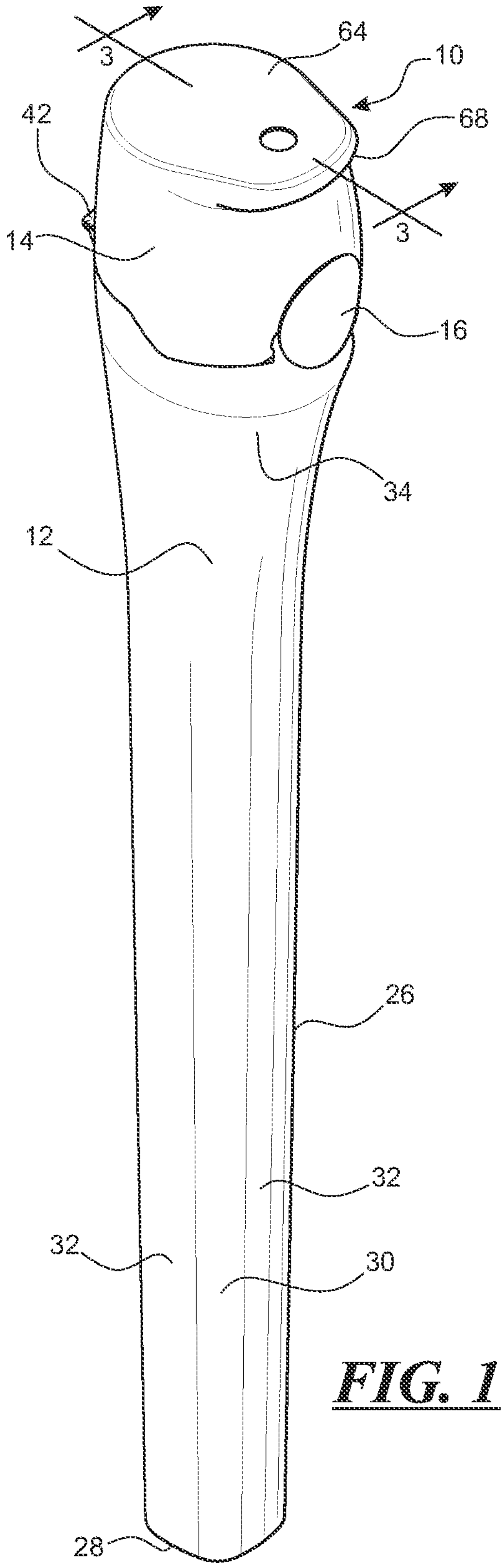
FIG. 1 is a perspective view of a medical product package with a first use indicator label applied thereon.
Figure 2:
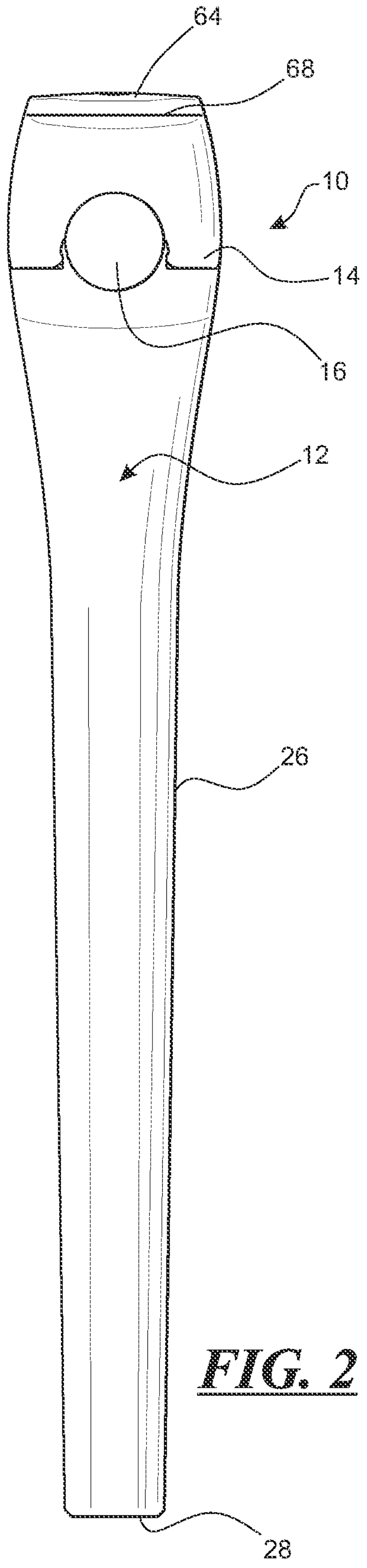
FIG. 2 is a front view of the medical product package of FIG. 1.

The present disclosure is directed to packages for medical products or devices such as intermittent urinary catheters. Such a package is shown generally at in FIGS. 1-2. FIGS. 1-2 show the major components of the package including: a case 12, a cap 14, and a first use indicator label 16. FIG. 3 illustrates the product contained within the package 10, namely, a urinary catheter 20 which includes catheter tubing 22 and a funnel 24 attached to one (distal) end of the tubing 22. Further details of the package and package and product are described in WO 2018/156589, the contents of which are incorporated herein by reference in their entirety.

The case is preferably molded from a suitable plastic material, such as polypropylene, although other materials could be used. The case includes a hollow tubular wall 26. Where the package is for housing a catheter or other elongated product, the tubular wall 26 terminates at an end wall 28 that closes the bottom of the tubular wall. The interior surface of the tubular wall may be generally cylindrical. The exterior surface of the tubular wall 26 may have either a cylindrical or rectangular cross-sectional shape or the cross-section could be otherwise. As shown in FIG. 1, most of the exterior surface of the tubular wall 26 has a generally rectangular cross-section with large-radiused corners 30 joining four sides 32, although as shown even the sides 32 are not perfectly flat as they have a slight curvature on their outer surfaces. Above this rectangular portion the tubular wall 26 flares outwardly somewhat at a neck portion 34 to increase the diameter of the tube.

Figure 6:
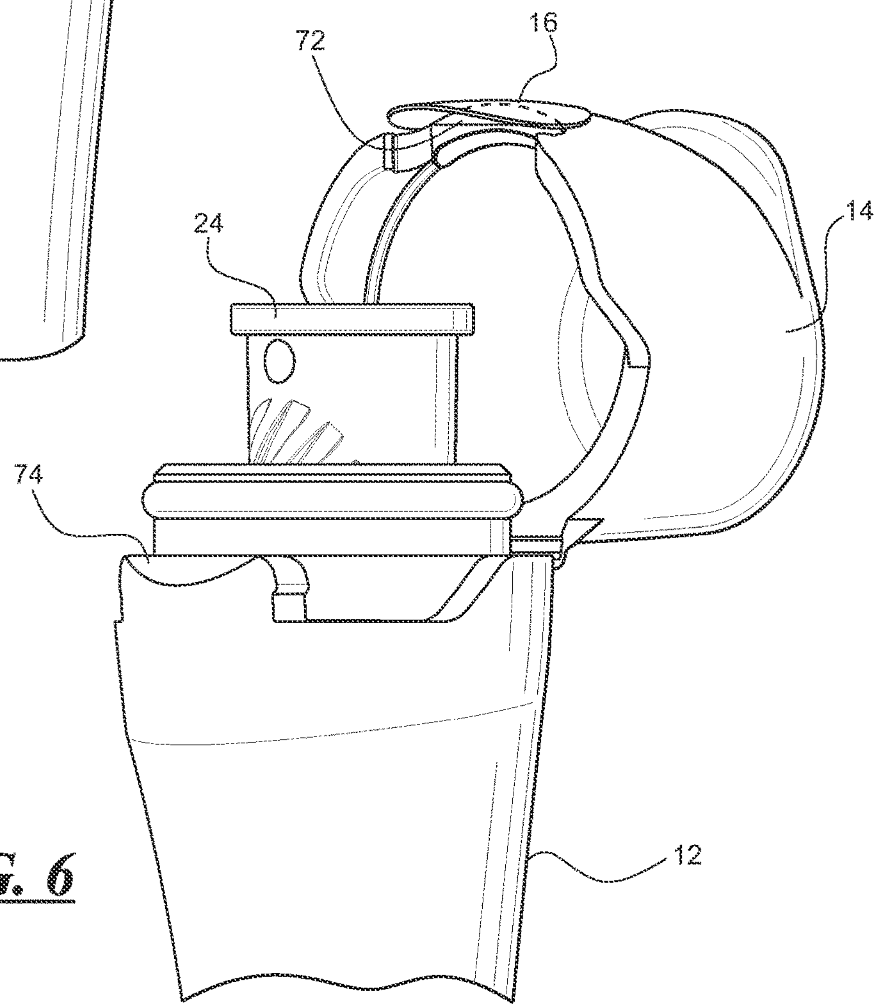
FIG. 6 is a partial perspective view of the medical product package with the cap opened.

Cap 14 is hinged to the case 12 by hinge 42 and is selectively movable by a user between a closed position and an open position. FIG. 6 shows the cap 14 in the open position. The cap 14 includes a generally cup-shaped shell having a top wall 64 joined to a generally cylindrical side wall or skirt 66. The top wall 64 and side wall 66 may merge on one side of the cap to form a lip 68 that makes it easy for a user to engage the cap with a finger or thumb. Alternately, the lip 68 can be used to assist in opening the cap by placing the lip 68 in engagement with the edge of a table or similar surface and pulling the case downwardly.

The hinge 42 as shown is preferably a living hinge of the butterfly type, but other hinge arrangements could be used. The hinge connects to the collar 36 and the cap 14 to permit selectable movement of the cap between open and closed positions.

As shown in FIGS. 1 and 2, a first use indicator label is located on the outer surface of package 10. In one embodiment, label 16 is placed over the junction of cap 14 and case 12, preferably directly opposite hinge 42. First use indicator label 16 may have a paper outer surface and an adhesive backing layer for affixation of label 16 to package 10. As will be described below, the material of label should be sufficiently strong to avoid tearing upon opening of the package (by flipping open cap 14). In addition, the adhesive on the back of label 16 should be such that the label is released from the case and remains intact during the opening sequence. The outer surface of label 16 may be blank or include a pattern or contrasting color to provide a further and clear affirmation of earlier use. The label shown in the Figures is shown as a circular label, but any shape may be used as long as label 16 spans the junction of the cap 14 and case 12 and the indentations which will now be described.

As will be appreciated from FIGS. 1 and 2 and as further described in \NO 2018/156589, [the outer surfaces or contours of the closed cap 14 and case 12 match one another at the junction line 15 where they meet. This provides a smooth, continuous outer contour to the package as a whole. There are no overlapping outer surfaces of the cap and case. There are no offsets, discontinuities, corners or exposed edges. This structure provides aesthetic benefits as well as the sealing benefits explained above. However, the smooth continuous outer contour also provides underlying support to the first use indication label 16.

Figure 5:
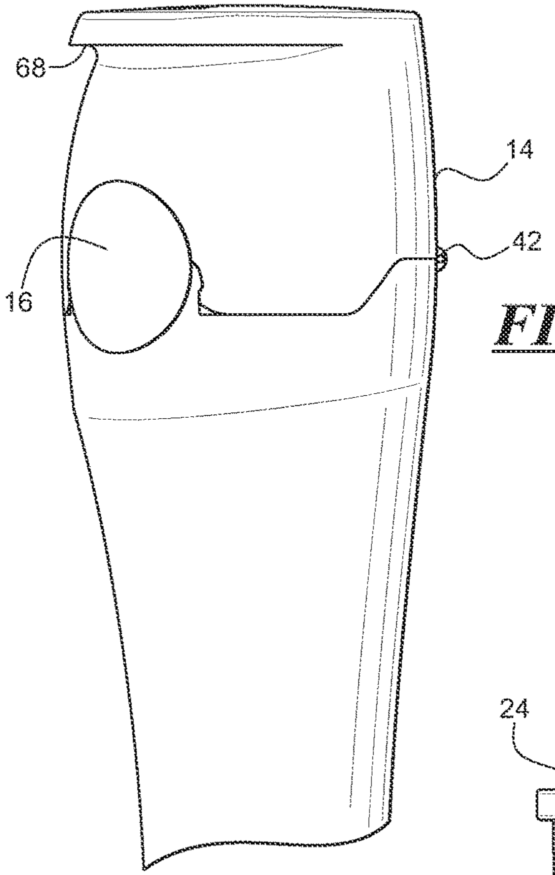
FIG. 5 is an enlarged perspective view of the medical product package with the first use indicator label placed thereon.

As shown in FIG. 4, an exception to the smooth continuous outer contour are an adjacent pair of indentations (or chamfers) 72 and 74 in each of the case 12 and cap 14. Each indentation is located along junction line 15 and defines an angled surface. A preferred circumferential location of the indentations 72 and 74 is centered 180° from the center of the hinge 42, i.e., at the front of the case, However, other locations for the indentations are possible. Mile angled chamfers as shown in FIG. 4 provide a convenient shape for creating an indentation or unsupported region under a first use indicator label, other arrangements are possible, such as a square or rectangular notch. Whatever the shape and location of the indentations, they create a depression 75 compared to the structure surrounding it and the first use indication label will span or overlie this depression or unsupported area. As seen in FIG. 5, first use indicator label 16 covers both indentations or chamfers and the depression 75 prior to the first use. The original and unaltered label shape (such as the circle in FIG. 5) provides evidence to the user that the package has not been previously opened.

In one embodiment, the size or area of the indentations 72 and 74 may be the same. Alternatively, lower indentation 74 may be greater in size (height, area) than the top indentation

72. This results in a greater surface area for the label 16 to adhere on the cap 14, rather than on the case 12, and further ensures that the label will remain with the cap 14 when opened (rather than remaining with the case 12).

Figure 8:
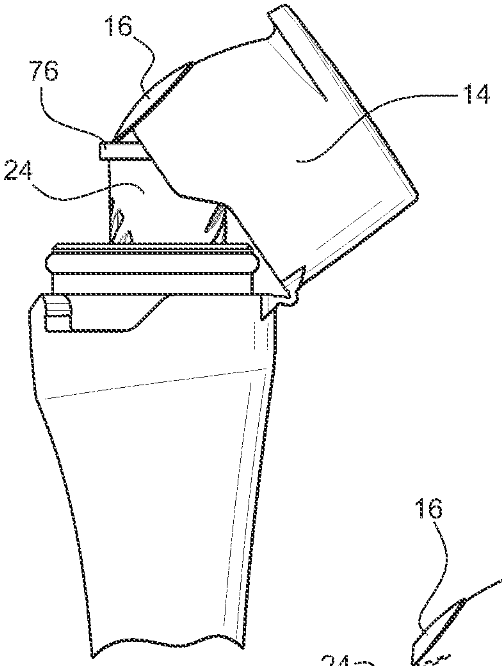
FIG. 8 is a partial side view of the medical product with the cap moved to a partially closed position.

As best seen in FIGS. 8 and 10, the position of the label 16 may be raised slightly such that an increased proportion of label 16 is adhered to the cap 14 rather than the case 12. Upon opening of the case, the higher positioned label will remain adhered to the cap rather than to the case. Such placement of label 16 may be particularly advantageous when indentations 72 and 74 are of same or similar size.

Packages of the type described herein are particularly useful for housing catheters such as intermittent urinary catheters. Turning briefly to FIG. 3, an intermittent urinary catheter 20 within package 10 is shown. Catheter 20 is secured within package 10 from which it can be removed by the user at the time of use. Distal funnel 24 extends beyond the opening in case 12 (best seen in FIG. 6) where it can be gripped by the user and removed from the case.

After use of the catheter 20, it is not uncommon for users to return the used catheter 20 to its package for disposal of the catheter and the package. Faced with a package that contains a catheter, the user would like to know whether the package has been previously opened (whether or not used).

Figure 7:
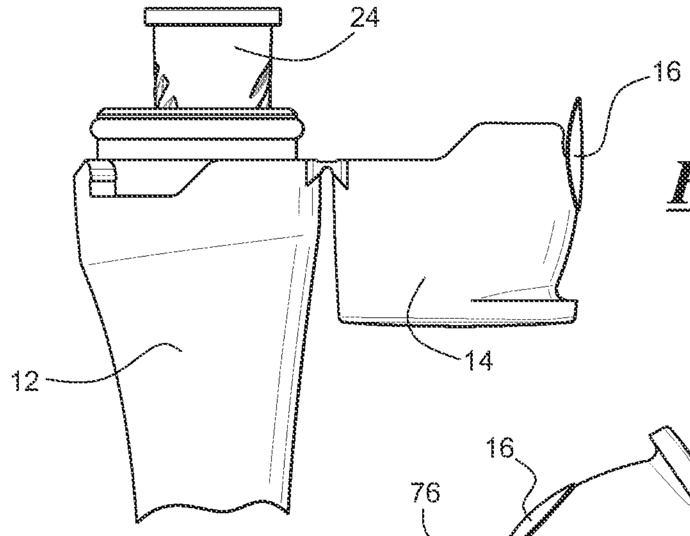
FIG. 7 is a partial side view of the medical product with the cap of the package in the fully opened position.

FIGS. 7-12 show the manner by which first use indication label 16 provides evidence that the package has been opened. FIG. 7 shows package 10 in its (fully) opened position with cap 14 rotated with distal funnel 24 of an intermittent urinary catheter exposed, secured within case 12 and extending beyond the opening of case 12. First use indicator label has been detached from the surface of case 12 but remains affixed to cap 14 intact with lower portion (that was previously affixed to case 12) depends from cap 14.

Figure 9:
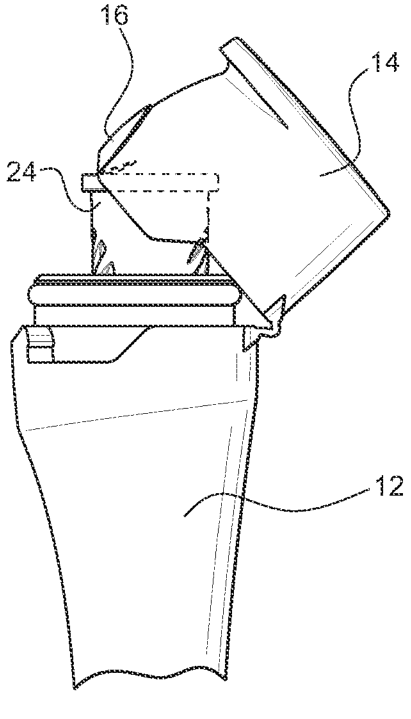
FIG. 9 is a partial side view of the medical product with the cap further moved to a partially closed position and the first use indicator label partially folded under the cap.

As shown in FIG. 8, rotating cap 14 from its open position of FIG. 7 toward a closed position causes the lower portion of label 16, and more particularly, lower edge 76 of label 16 to contact funnel 24. In this regard, funnel 24 is positioned within case 12 such that contact between the funnel (or funnel flange 78) occurs. As label 16 contacts funnel 24, the lower half of label 16 is folded inwardly over indentation 72 as shown in FIGS. 9 and 10. As cap 14 clears the funnel 24, label 16 is now folded under the lower edge of cap 14 and indentation 72 resulting in something less than the full label 16. This is perhaps best seen when comparing the label 16 in FIG. 2 to the label in FIGS. 11 and 12. The full circle label of FIG. 2 prior to initial opening becomes a recognizable and unmistakable "half-moon" label after it has been open and then reclosed.

The embodiments disclosed herein are for the purpose of providing a description of the present subject matter, and it is understood that the subject matter may be embodied in various other forms and combinations. Therefore, the specific embodiments and features disclosed herein are not to be interpreted as limiting the subject matter as defined by the accompanying claims.

The invention claimed is:

1. A medical product assembly comprising;

a) a package, the package including a case for receiving a medical product, the case having an open end, a cap for sealing the open end of the case, a hinge having a first end connected to the cap and a second end connected to the case, an indentation in an outer surface of the cap, the indentation in a portion of the outer surface of the cap having a reduced outer dimension compared to a remaining portion of the outer surface of the cap in which it is formed, an indentation in an outer surface of the case, the indentation in a portion of the outer surface of the case having a reduced outer dimension compared to a remaining portion of the outer surface of the case in which it is formed, the indentation in the cap and the indentation in the case being adjacent to each other when the cap is in a fully closed position; and a first use indication label affixed to the cap and case that spans both the indentation in the cap and the indentation in the case when the cap is in the fully closed position; and b) a medical device contained within the package, the medical device having a distal end that extends beyond the open end of the case and positioned within the case such that the first use indication label contacts the distal end of the medical device when the cap is moved from an open position to a re-closed position.

2. The medical product assembly of claim 1 wherein the medical device is positioned within the case such that a lower portion of said first use indication label folds upon contact with the distal end of the medical device.

3. The medical product assembly of claim 1 wherein the medical device is positioned within the case such that a lower portion of the first use indication label folds upon contact with the distal end of the medical device without preventing closure of the case with the cap.

4. The medical product assembly of claim 1 wherein the cap comprises a shell having a top wall and skirt depending from the peripheral edge of the top wall, the shell defining an interior chamber for receiving the distal end of the device that extends beyond the open end of the case.

5. The medical product assembly of claim 1 wherein in an open position a top portion of the first use indication label remains affixed to the cap and a bottom portion of the first use indication label depends from the top portion.

6. The medical product assembly of claim 5 wherein the bottom portion of the first use indication label depends from a bottom portion of the shell.

* * * * *